(12) United States Patent
Otsubo

(10) Patent No.: US 6,497,693 B1
(45) Date of Patent: Dec. 24, 2002

(54) DISPOSABLE UNDERGARMENT

(75) Inventor: Toshifumi Otsubo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/518,077

(22) Filed: Mar. 3, 2000

(30) Foreign Application Priority Data

Mar. 5, 1999 (JP) .......................................... 11-058646

(51) Int. Cl.⁷ .......................... A61F 13/15; A61F 13/20
(52) U.S. Cl. ......................... 604/385.19; 604/385.101; 604/385.28; 604/385.29; 604/398; 604/402
(58) Field of Search ..................... 604/385.01, 385.101, 604/385.19, 385.201, 385.24–385.3, 386, 393, 394, 397–402

(56) References Cited

U.S. PATENT DOCUMENTS

| | | | | |
|---|---|---|---|---|
| 3,322,122 A | * | 5/1967 | Daniel | 604/385.01 |
| 3,884,234 A | * | 5/1975 | Taylor | 604/385.201 |
| 4,560,380 A | * | 12/1985 | Tharel | 604/385.19 |
| 4,935,021 A | | 6/1990 | Huffman et al. | |
| 4,946,454 A | * | 8/1990 | Schmidt | 604/385.19 |
| 5,062,840 A | * | 11/1991 | Holt et al. | 604/385.19 |
| 5,624,422 A | | 4/1997 | Allen | |
| 5,653,842 A | * | 8/1997 | Kuen | 604/385.19 |
| 5,746,730 A | | 5/1998 | Suzuki et al. | |
| 5,853,405 A | | 12/1998 | Suprise | |
| 6,406,465 B1 | * | 6/2002 | Otsubo | 604/378 |

FOREIGN PATENT DOCUMENTS

| | | |
|---|---|---|
| GB | 2 262 873 | 7/1993 |
| JP | 6-21624 | 3/1994 |
| JP | 7-7620 | 2/1995 |
| WO | 98/16179 | 4/1998 |

* cited by examiner

Primary Examiner—Glenn K. Dawson
Assistant Examiner—K. M. Reichle
(74) Attorney, Agent, or Firm—Lowe Hauptman; Gilman & Berner, LLP

(57) ABSTRACT

A disposable undergarment such as a disposable diaper includes a front waist region, a rear waist region and a crotch region extending therebetween, the undergarment has afterward bonded edges extending along a longitudinal center line of the rear waist region and a concavity depressed toward a surface destined to be remote from the wearer's skin, the rear waist region is divided into a first rear waist region and a second rear waist region along a longitudinal center line extending in the longitudinal direction to bisect a transverse dimension of the undergarment, and the concavity is formed by drawing the first rear waist region and the second waist region toward each other and bonding the afterward bonded edges to each other on the longitudinal center line.

5 Claims, 5 Drawing Sheets

DISPOSABLE UNDERGARMENT

BACKGROUND OF THE INVENTION

This invention relates to disposable undergarments such as diaper covers, disposable diapers or the like.

Japanese Utility Model Application Gazette No. 1995-7620 discloses a disposable diaper comprising a liquid pervious topsheet, a liquid-impervious backsheet and a liquid-absorbent core disposed between these two sheets. The topsheet is provided in the middle zone of the crotch region with a liquid-absorbent annular member which is, in turn, covered with a liquid-pervious cover sheet so that the annular member cooperates with a section of the topsheet encircled by the annular member to form an excrement receiving concavity.

Japanese Utility Model Application Disclosure No. 1994-21624 discloses a disposable diaper comprising a liquid pervious topsheet, a liquid-impervious backsheet and an absorbent core disposed between these two sheets. The absorbent core is provided in its hip region with a concavity serving to receive excrement disposed onto the diaper.

Both of the proposals intend to form the absorbent core with a concavity serving to receive solid excretion such as faeces therein with or without a annular protuberance encircling it.

However, various problems may be encountered by such known diapers depending on situations. Assume that the excrement receiving concavity formed in the crotch region or the excrement receiving concavity formed in the hip region misses the proper position to receive the excrement. In this case, the solid excretion can not be received by the concavities.

With the diaper described in Japanese Utility Model Application Disclosure No. 1995-7620, the annular member overlies the absorbent core and increases a thickness of the diaper. The increased thickness of the diaper creates an uncomfortable feeling for the wearer.

In the case of the diaper described in Japanese Utility Model Application Disclosure No. 1994-21624, if the liquid-permeability of the topsheet defining the upper surface of the diaper is not sufficient, the fluid excretion such as loose passage due to diarrhea once having been received by the concavity may flow back again up to the surface of the topsheet and spread sideways.

If the absorbent core is relatively thin as achieved by recent technical progress, it will be difficult to form the concavity adapted to receive a desired amount of excrement.

SUMMARY OF THE INVENTION

The above and other objects of the present invention are achieved by a disposable undergarment having along a longitudinal direction thereof a front waist region, a rear waist region and a crotch region therebetween. The undergarment comprises a concavity depressed toward a surface destined to be remote from a wearer's skin as the undergarment is put on the wearer's body. The undergarment is made from a panel, which has, in the rear waist region, an afterward bonded edge extending transverse to the longitudinal direction along an end of the panel and being divided by a longitudinal center line of the undergarment into first and second bonded edges. The undergarment is made by bonding the first and second bonded edges of the panel to each other along the longitudinal center line, thereby forming the concavity.

In accordance with one aspect of the present invention, the panel, in the rear waist region, comprises a central portion having the longitudinal center line and first and second wings extending transversely outwardly from opposite sides of the central portion so that the first and second bonded edges of the panel extend continuously from the longitudinal center line into the first and second wings, respectively. Portions of the first and second bonded edges in the first and second wings, respectively, are bonded to each other along the longitudinal center line so as to form the concavity of the undergarment.

In accordance with another aspect of the present invention, the panel is a laminate panel comprising a liquid-pervious topsheet and a liquid-impervious backsheet both extending over the front and rear waist regions as well as the crotch region and the first and second wings, and a liquid-absorbent core disposed between the topsheet and the backsheet.

In accordance with a further aspect of the present invention, the laminate panel further comprises a pair of barrier cuffs extending between transversely opposite side edges of the crotch region and from the front waist region to the rear waist region in the longitudinal direction. The barrier cuffs are biased to rise on an upper surface of the topsheet. Each of the barrier cuffs has a free distal edge being biased away from the upper surface of the topsheet, a proximal edge being bonded to the upper surface of the topsheet, and longitudinally opposite ends respectively lying in the front and rear waist regions. The longitudinally opposite ends of the barrier cuffs which lie in the rear waist region are bonded together along the afterward bonded edge so that the barrier cuffs come in contact with each other in the rear waist region.

In accordance with yet another aspect of the present invention, the longitudinally opposite ends of the barrier cuffs are bonded to the upper surface of the topsheet so that the longitudinally opposite ends are maintained collapsed towards the longitudinal center line of the undergarment.

DETAILED DESCRIPTION OF THE PREFERRED EMBODIMENTS

Details of an undergarment according to this invention will be more fully understood from the following description of a so-called open-type disposable diaper made from a laminate panel with reference to the accompanying drawings.

Figure 1:
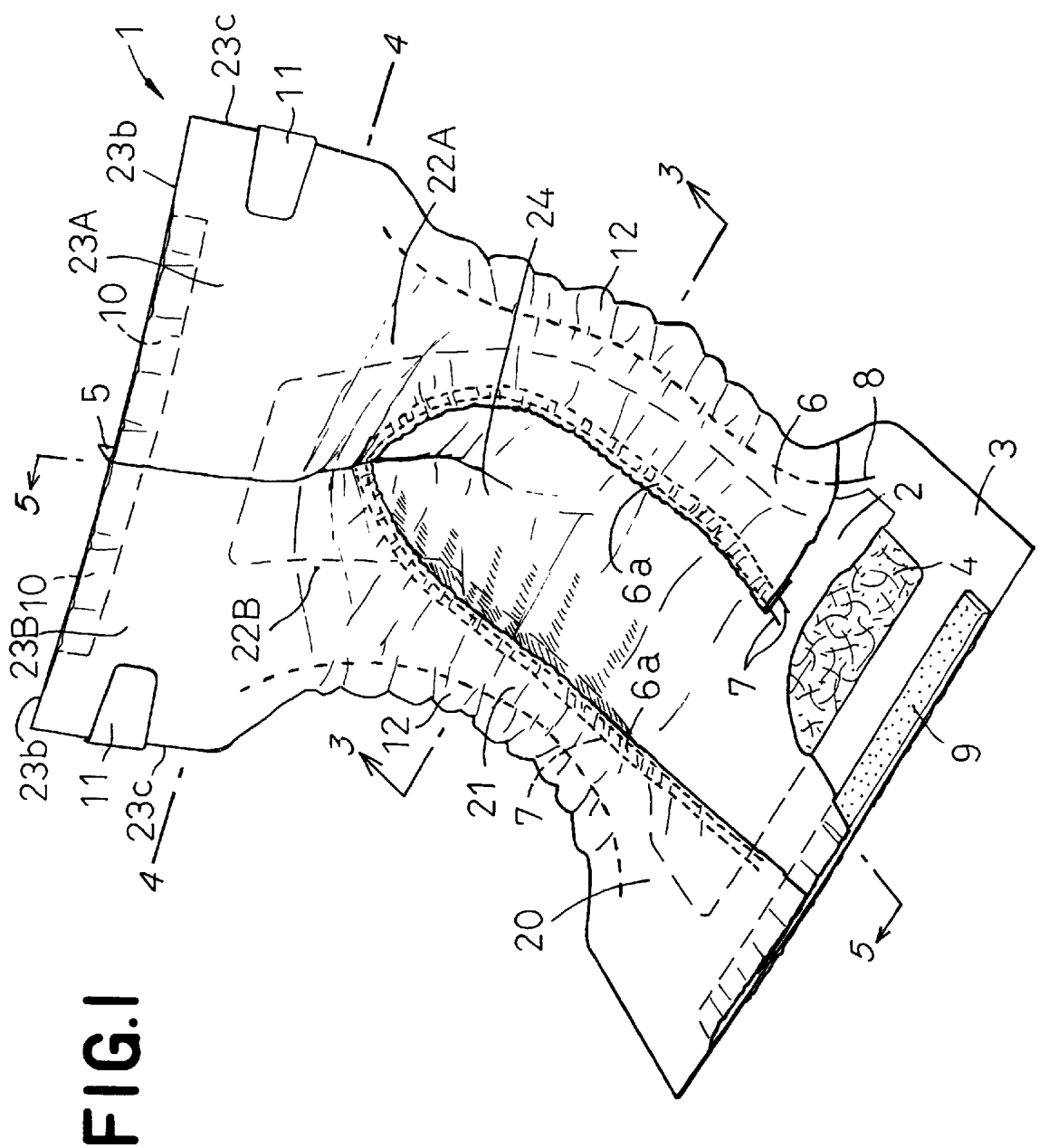
FIG. 1 is a perspective view showing a partially cutaway undergarment according to this invention, the undergarment being made from a laminate panel.

FIG. 1 is a perspective view showing a partially cutaway undergarment 1. The undergarment 1 comprises a liquid-pervious topsheet 2, a liquid-impervious backsheet 3 and a liquid-absorbent core 4 disposed between the two sheets 2, 3 and bonded to the inner surface of at least one of the two sheets 2, 3. The undergarment 1 is contoured by transversely opposite side edges extending in the longitudinal direction and longitudinally opposite ends extending in the transverse direction intersecting the longitudinal direction.

The undergarment 1 is provided with a pair of barrier cuffs 6 extending longitudinally of the undergarment 1. Each of the cuffs 6 is formed with a liquid-impervious nonwoven fabric sheet and provided along its free side edge 6a with an elastic member 7 secured under tension thereto. The undergarment 1 is formed in its zone covering the wearer's hip with a concavity 24 depressed toward the surface of the undergarment 1 remote from the wearer's skin so that the pair of barrier cuffs 6 may come in contact with each other above the concavity 24 and thereby enclose the concavity 24.

The undergarment 1 is further formed with a pair of side flaps 12 laterally extending outward from transversely opposite side edges of the absorbent core 4. In addition, the undergarment 1 is provided along its transversely opposite side edges, which are intended to form a pair of leg-openings, with elastic members 8 extending in the longitudinal direction and secured under tension thereto. Similarly, the longitudinally opposite ends of the undergarment 1, which are intended to define a waist-opening, are provided with film-like elastic members 9, 10 extending in the transverse direction and under tension thereto so as to be associated with the waist-opening.

Upon relaxation of the elastic members 8, 9, 10, gathers are produced along the longitudinally opposite ends as well as along the transversely opposite side edges of the undergarment 1. When the undergarment 1 is longitudinally curved with its inner surface inside, contraction of the elastic members 7 causes the barrier cuffs 6 to rise on the upper surface of the undergarment 1 and creates gathers along the free side edges 6a of the respective barrier cuffs 6.

Figure 2:
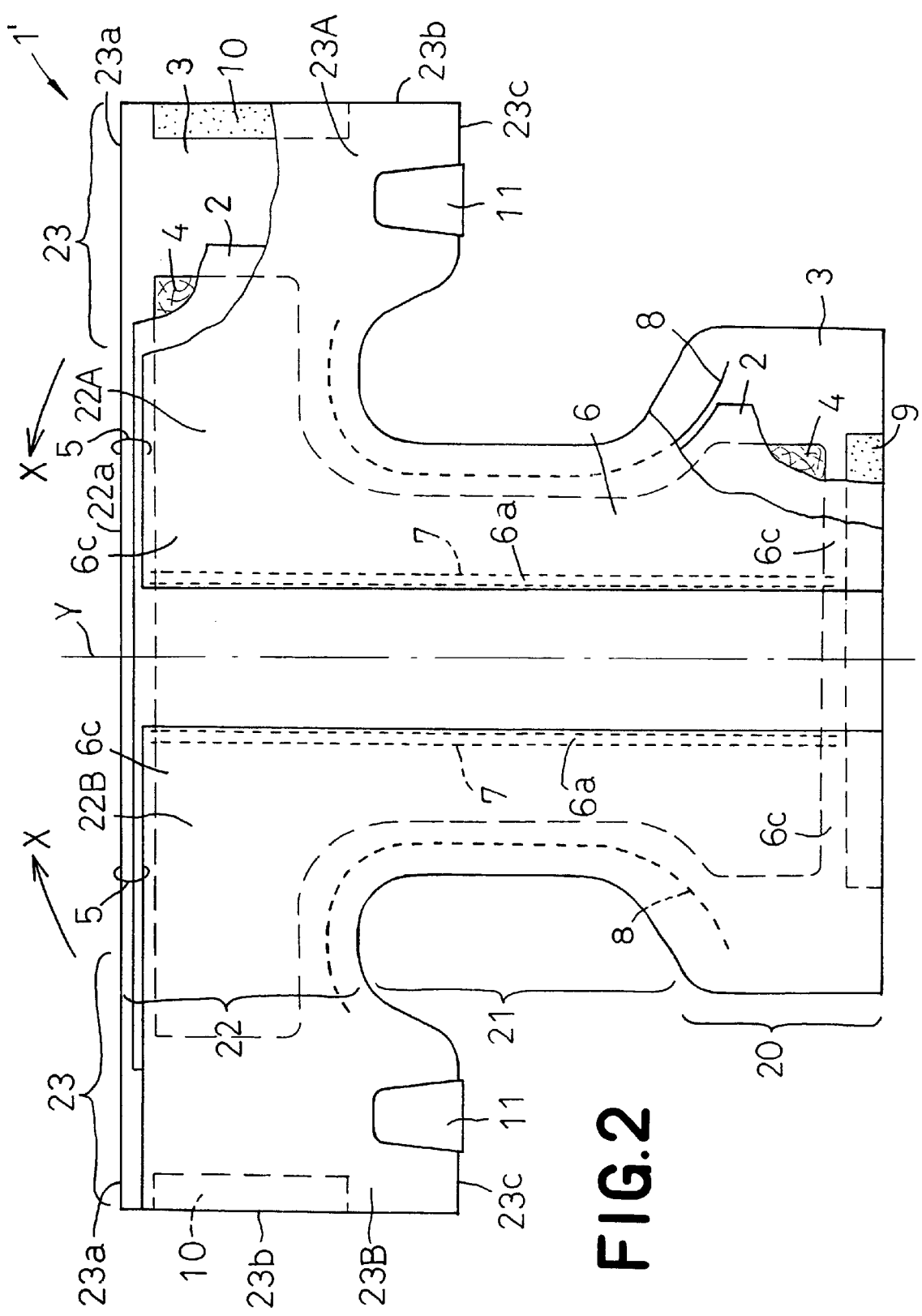
FIG. 2 is a plan view showing the partially cutaway panel before a concavity is formed to obtain the undergarment.

FIG. 2 is a partially broken plan view showing a panel 1' before the concavity 24 is formed to obtain the undergarment 1. Identical elements of panel 1' and undergarment 1 are denoted by identical reference numerals. As shown, the panel 1' comprises a front waist region 20, a rear waist region 22 and a crotch region 21 extending between the front and rear waist regions 20, 22 as viewed longitudinally of the panel 1'. The panel 1' further comprises a pair of wings 23 extending outward from transversely opposite side edges of the rear waist region 22.

Along longitudinal ends 22a, 23a of the rear waist region and wings 22, 23, the panel 1' has a pair of afterward bonded edges 5. Along the afterward bonded edges 5, the backsheet 3 longitudinally extends beyond the topsheet 2 which, in turn, longitudinally extends beyond the barrier cuffs 6.

The panel 1' has a longitudinal center line Y bisecting a transverse dimension of the panel 1'. About the longitudinal center line Y, the rear waist region 22 is divided into first and second rear waist regions 22A, 22B and the wings 23 are divided into first and second wings 23A, 23B. The first and second rear waist regions 22A, 22B and first and second wings 23A, 23B are respectively drawn near together in directions as indicated by arrows X, X and the afterward bonded edges 5, 5 are bonded to each other. In consequence, the undergarment 1 is formed with the concavity 24. Now edges 23c of the respective wings 23 lying symmetrically about the longitudinal center line partially form the transversely opposite side edges of the undergarment 1 and outer side edges 23b of the respective wings 23 form one of the longitudinally opposite ends of the undergarment 1 (See FIG. 1).

The wings are formed with portions of the topsheet 2, the backsheet 3 and the barrier cuffs 6. The absorbent core 4 is disposed between portions of the topsheet 2 and the backsheet 3. In the respective wings 23, the topsheet 2 extends outward slightly beyond the transversely opposite side edges of the absorbent core 4 and the portions of backsheet 3 transversely extending beyond the tops beet 2 are bonded to the corresponding portions of barrier cuffs 6.

The transversely opposite, i.e., longitudinally extending side edges 23b of the wings 23 are provided with the elastic members 10 longitudinally extending along these side edges 23b. The elastic members 10 are disposed between the backsheet 3 and the barrier cuffs 6 and secured to at least one of the backsheet 3 and barrier cuffs 6. The lower ends 23c of the respective wings 23, which transversely extend in parallel to the afterward bonded edges 5, are provided with a pair of tape fasteners 11. The tape fasteners 11 have their free ends coated with adhesive agent and their proximal ends joined to the lower ends 23c.

Figure 3:
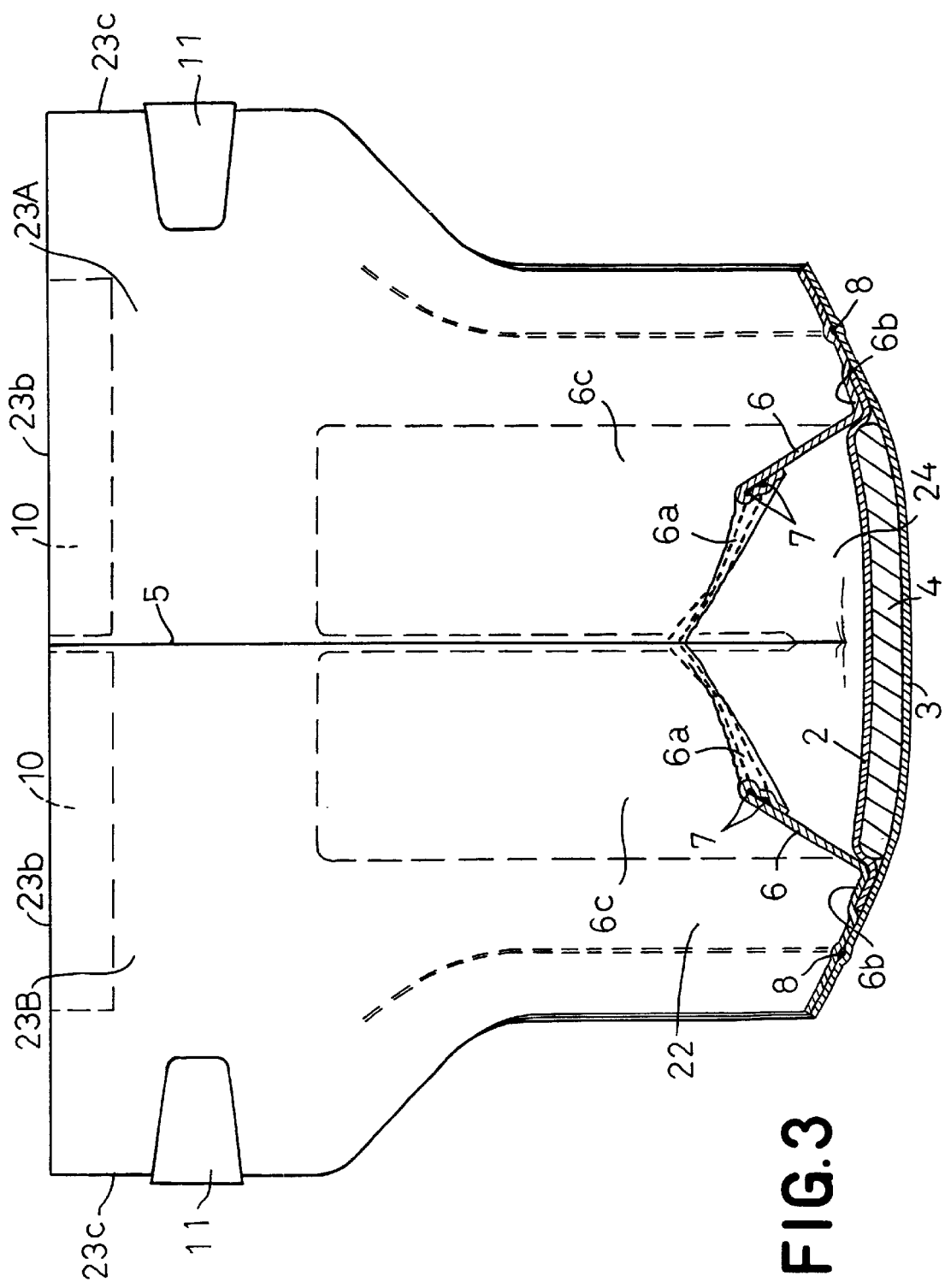
FIG. 3 is a plan view showing the undergarment partially in a sectional view taken along a line A—A in FIG. 1.
Figure 4:
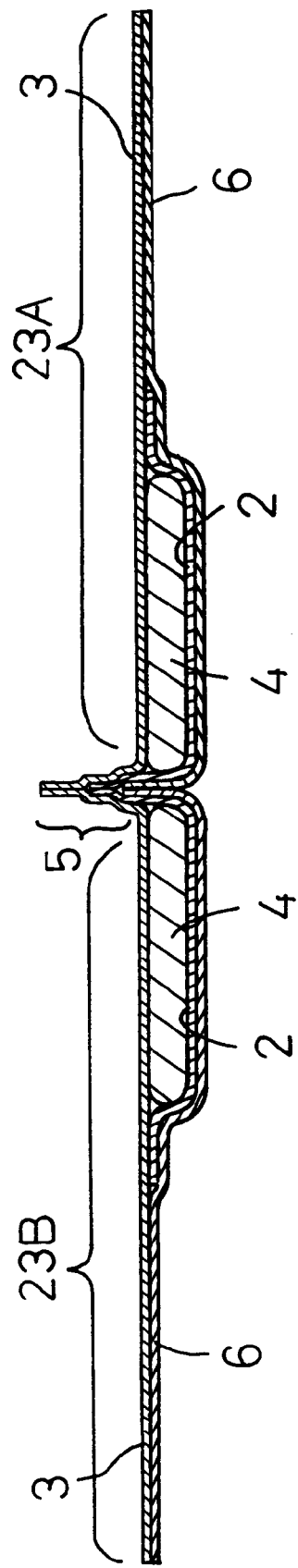
FIG. 4 is a sectional view taken along a line B—B in FIG. 1.

FIG. 3 is a plan view showing the undergarment 1 partially in a sectional view taken along line A—A in FIG. 1, and FIG. 4 is a sectional view taken along a line B—B in FIG. 1. FIG. 3 shows the barrier cuffs 6 as they rise on the inner surface of the undergarment 1. The transversely opposite side edges of the topsheet 2 extend outward slightly beyond the transversely opposite side edges of the absorbent core 4. The portions of the backsheet 3 transversely extending outward beyond the transversely opposite side edges of the topsheet 2 are bonded to the respective barrier cuffs 6 with the elastic members 8 disposed therebetween.

The barrier cuffs 6 have their proximal side edges 6b bonded to the upper surface of the topsheet 2 and their longitudinal ends 6c extending in the rear waist regions 22 as well as in the wing 23 are bonded to the upper surface of the topsheet 2 so that these ends 6c may be held to collapse inward of the undergarment 1 onto the upper surface of the topsheet 2. Along the free side edges 6a, the barrier cuffs 6 are folded back to wrap the elastic members 7 which are, in turn, intermittently bonded to the barrier cuffs 6.

Referring to FIG. 4, along the afterward bonded edges 5 extending in the region defined by the wings 23, the respective barrier cuffs 6 associated with the first and second wings 23A, 23B have their upper surfaces put flat and bonded together. Similarly, the sections of the topsheet 2 associated with the first and second wings 23A, 23B and extending upward beyond the barrier cuffs 6 as viewed in FIG. 4 have their upper surfaces put flat and bonded together. The sections of the backsheet 3 extending upward beyond the topsheet 2 as viewed in FIG. 4 also have their upper surfaces put flat and bonded together.

Figure 5:
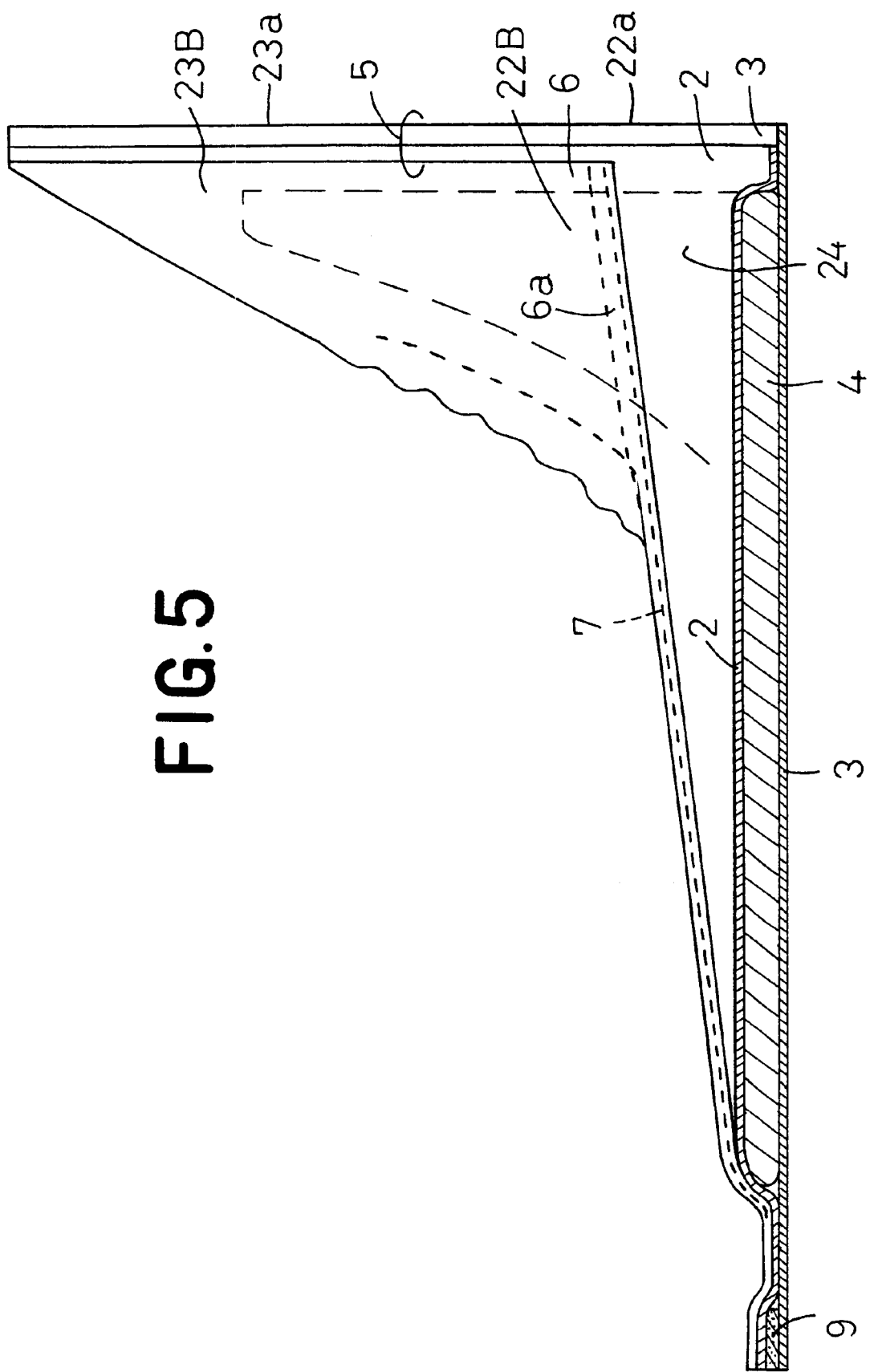
FIG. 5 is a sectional view taken along a line C—C in FIG. 1.

FIG. 5 is a sectional view taken along a line C—C in FIG. 1. As shown, the undergarment 1 has a substantially L-shaped section defined by the rear waist region 22 and the wings 23 rising with respect to the front waist region 20 and the crotch region 21. The concavity 24 has the maximum depth substantially in a middle zone of the bonded edge 5.

In the front waist region 20, the outer surface of the undergarment 1 is provided with a pair of fastening zones each in the form of a target tape so that the respective tape fasteners may be fastened to the corresponding target tape by means of the adhesive agent applied on the inner surfaces of the tape fasteners. In this manner, a waist-opening and a pair of leg-openings are formed (not shown).

Excretion is first absorbed by a portion of the absorbent core 4 lying in the front waist region 20, the crotch region 21 and the rear waist region 22, and then exudes into a portion of the absorbent core 4 lying in the wings 23 to be absorbed therein. Compared to the case in which no portion of the absorbent core 4 is present in the wings 23, the amount of excretion which can be absorbed by the core 4 is correspondingly increased. Even if the portion of the absorbent core 4 lying in the wings 23 is compressed by the back of the undergarment wearer, it is not a concern that the amount of excretion once absorbed by the portion of the core 4 lying in the wings 23 might exude again on the upper surface of the undergarment 1 because the upper surfaces of the wings 23 are covered with the respective barrier cuffs 6. The portion of the absorbent core 4 additionally serves as a cushion and thereby contributes to an improved feel while wearing the undergarment.

The topsheet 2 may be formed by a liquid-pervious sheet such as nonwoven fabric or porous plastic film, preferably a sheet which is not only liquid-pervious but also hydrophobic. The backsheet 3 may be formed with a liquid-impervious plastic film or a laminate of such plastic film and a hydrophobic nonwoven fabric, preferably a breathable and liquid-impervious sheet. The barrier cuffs 6 may be formed with a breathable nonwoven fabric or a breathable, liquid-impervious and stretchable nonwoven fabric sheet. When the stretchable nonwoven fabric sheet is used as the stock material for the barrier cuffs 6, the barrier cuffs 6 may be secured under tension to the upper surface of the panel 1 and eliminate the need to provide the free side edges 6a of the respective barrier cuffs 6 with the elastic members 7. The nonwoven fabric may be selected from a group consisting of a spun bond nonwoven fabric, a spun lace nonwoven fabric and a melt blown nonwoven fabric, each comprising fibers having a basis weight of 5~150 g/m2. The absorbent core 4 comprises a mixture of fluff pulp and superabsorptive polymer particles compressed to a desired thickness and entirely covered with a water-pervious sheet such as tissue paper. Bonding of these members may be performed by means of suitable adhesive agents such as hot melt adhesive, glue or heat-sealing technique.

This invention is applicable not only to a so-called open type disposable diaper but also to the other articles such as a diaper cover or a pants type disposable diaper. In the case of the diaper cover, for example, a liquid-impervious plastic film or a laminate of such plastic film and a hydrophobic nonwoven fabric may used to form the diaper cover and a liquid-absorbent pad may be placed in the concavity 24 of this cover.

The undergarment proposed by this invention enables the formation of a concavity serving to receive and retain discharged excretion within the undergarment without use of an annular member to form the excrement receiving concavity or forming the liquid-absorbent core itself with the excrement receiving concavity. Compared to known excrement receiving concavities, this invention enables the concavity to have a large range in the rear waist region as well as in the crotch region. Advantageously, excrement can be reliably received by the concavity even if a position at which the excrement is discharged shifts rearwardly, forwardly or laterally relative to the wearer's body.

If excretion is solid, such excretion will directly fall into the concavity and will neither flow back nor leak from the undergarment. Even if excretion is fluid, such excretion will be absorbed by the absorbent core through the topsheet and neither flow back to the upper surface nor spread thereon. Above the concavity, the pair of barrier cuffs are in contact with each other to enclose the concavity so that these cuffs function as barriers to prevent the excretion from leaking.

What is claimed is:

1. A disposable undergarment having along a longitudinal direction thereof a front waist region, a rear waist region and a crotch region therebetween, said undergarment comprising a concavity depressed toward a surface destined to be remote from a wearer's skin as said undergarment is put on the wearer's body, wherein said undergarment is made from a panel, which has, in said rear waist region, an afterward bonded edge extending transverse to the longitudinal direction along an end of said panel and being divided by a longitudinal center line of said undergarment into first and second bonded edges; and said undergarment is made by bonding the first and second bonded edges of said panel to each other along the longitudinal center line, thereby forming said concavity.

2. The disposable undergarment according to claim 1, wherein said panel, in said rear waist region, comprises a central portion having the longitudinal center line and first and second wings extending transversely outwardly from opposite sides of the central portion so that the first and second bonded edges of said panel extend continuously from the longitudinal center line into the first and second wings, respectively; and portions of the first and second bonded edges in the first and second wings, respectively, are bonded to each other along the longitudinal center line so as to form said concavity of said undergarment.

3. The disposable undergarment according to claim 2, wherein said panel is a laminate panel comprising a liquid-pervious topsheet and a liquid-impervious backsheet both extending over said front and rear waist regions as well as said crotch region and said first and second wings, and a liquid-absorbent core disposed between said topsheet and said backsheet.

4. The disposable undergarment according to claim 3, wherein said laminate panel further comprises a pair of barrier cuffs extending between transversely opposite side edges of said crotch region and from said front waist region to said rear waist region in the longitudinal direction, said barrier cuffs being biased to rise on an upper surface of said topsheet, each of said barrier cuffs having a free distal edge being biased away from the upper surface of said topsheet, a proximal edge being bonded to the upper surface of said topsheet, and longitudinally opposite ends respectively lying in said front and rear waist regions, the longitudinally opposite ends of said barrier cuffs which lie in said rear waist region being bonded together along said afterward bonded edge so that said barrier cuffs come in contact with each other in said rear waist region.

5. The disposable undergarment according to claim 4, wherein said longitudinally opposite ends of said barrier cuffs are bonded to the upper surface of said topsheet so that said longitudinally opposite ends are maintained collapsed towards the longitudinal center line of said undergarment.

\* \* \* \* \*